Figure 2:
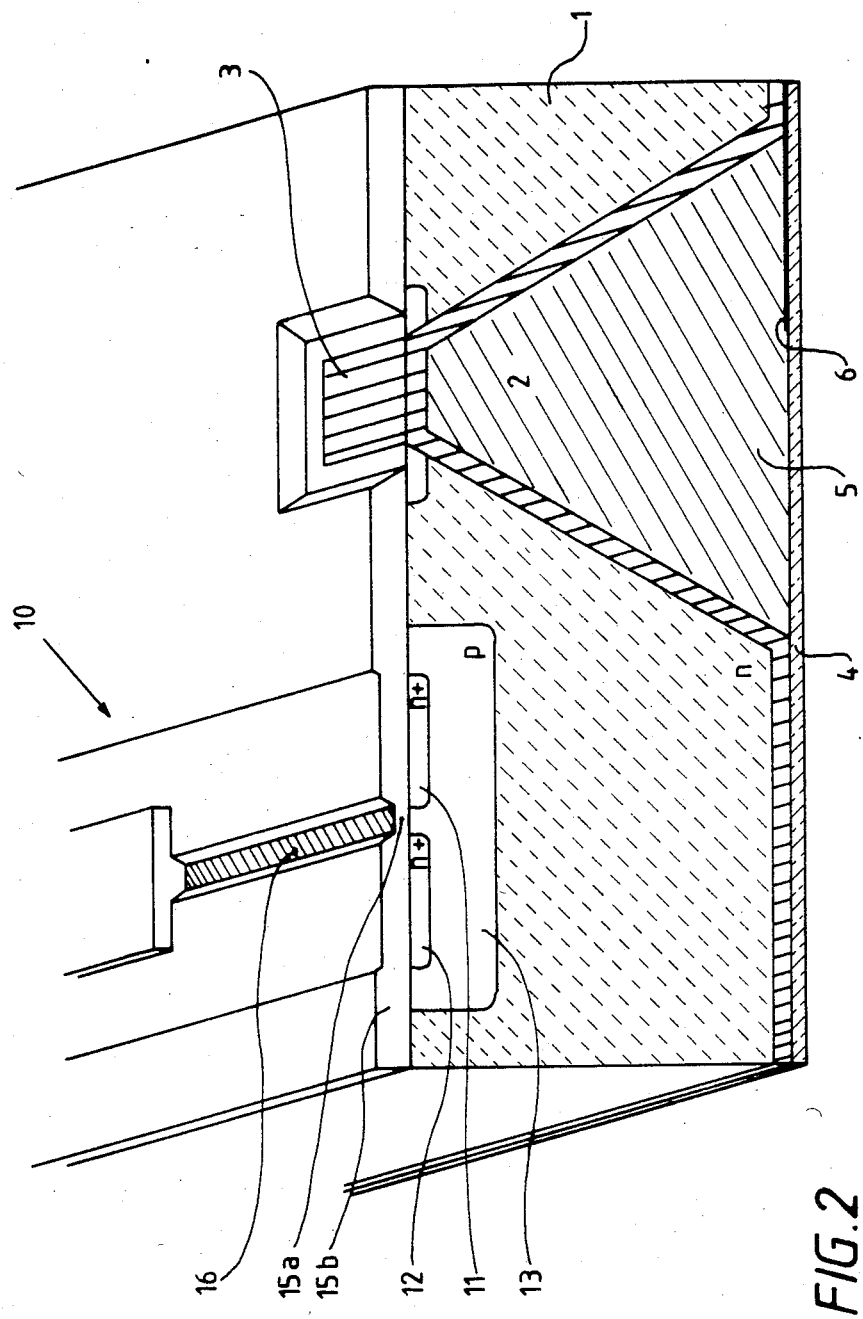

United States Patent [19]

Smith et al.

[11] Patent Number: 4,592,824
[45] Date of Patent: Jun. 3, 1986

[54] MINIATURE LIQUID JUNCTION REFERENCE ELECTRODE AND AN INTEGRATED SOLID STATE ELECTROCHEMICAL SENSOR INCLUDING THE SAME

[75] Inventors: Rosemary L. Smith, Neuchâtel, Switzerland; Scott Collins, Ogden, Utah

[73] Assignee: Centre Suisse d'Electronique et de Microtechnique S.A., Neuchâtel, Switzerland

[21] Appl. No.: 775,769

[22] Filed: Sep. 13, 1985

[51] Int. Cl.⁴ .................................... G01N 27/30
[52] U.S. Cl. .................................. 204/416; 128/635; 204/403; 204/435; 357/25
[58] Field of Search ............... 204/435, 416, 417, 418, 204/419, 420, 403; 357/25; 128/635

[56] References Cited

U.S. PATENT DOCUMENTS 2,925,370 2/1960 Rohrer .............................. 204/435
4,508,613 4/1985 Busta et al. ...................... 204/418

OTHER PUBLICATIONS

Implantable Ion Sensitive Transistors, by Harame et al., Frontiers in Medicine, Sep. 1984.
A Field Effect Transistor as a Solid State Reference Electrode by Comte et al.14 1979.
An Implantable Ion Sensor Transducer, by Harame et al., 1981.

Primary Examiner—G. L. Kaplan
Attorney, Agent, or Firm—Parkhurst & Oliff

[57] ABSTRACT

This invention relates to a miniature reference electrode of the liquid junction-type which is utilized by an integrated electrochemical sensor, which functions as an Ion Sensitive Field Effect Transistor.

8 Claims, 3 Drawing Figures

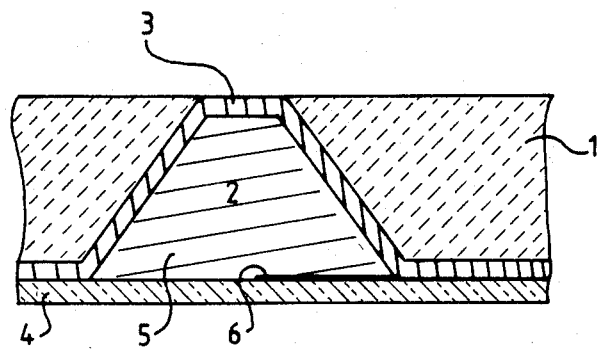
FIG.1.a
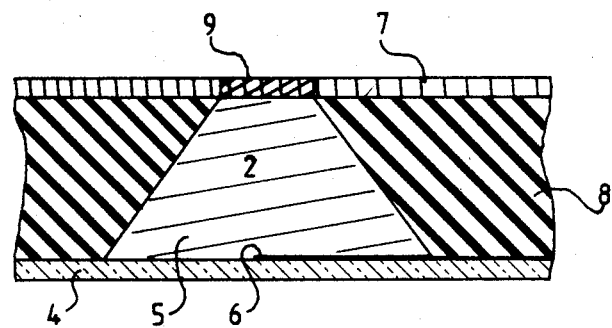
FIG.1.b

MINIATURE LIQUID JUNCTION REFERENCE ELECTRODE AND AN INTEGRATED SOLID STATE ELECTROCHEMICAL SENSOR INCLUDING THE SAME

BACKGROUND OF THE INVENTION

The present invention relates generally to integrated biochemical sensors and especially relates to a miniature reference electrode of the liquid junction type and an integrated solid state electrochemical sensor making use of such a reference electrode.

Much of the recent literature on new electrochemical sensors has centered on the application or development of chemically sensitive semiconductor devices, with ISFET's (Ion Sensitive Field Effect Transistors) enjoying a predominate role. The solid state construction of these devices makes them attractive for biochemical sensing for several reasons: (1) They are batch fabricated in silicon, using planar integrated circuit technology, which reduces individual cost and variations in device characteristics. (2) They offer the possibility of "smart" multisensors, allowing for on-site signal processing. (3) They are rugged yet very small, which is an ideal combination for in vivo applications. Despite these advantageous characteristics, the development of commercially available sensors has been hampered by some very basic technological problems.

One of the problems that has restricted the use of ISFET's as a viable biomedical sensor has been the unavailablity of a suitable solid state reference electrode. A true solid state reference electrode would comprise a material whose interfacial potential remains invariant for different electrolytes and varying concentrations of aqueous electrolyte. A few attempts to discover such an electrochemical material have been proposed, (for instance in U.S. Pat. No. 4,269,682), with varying degrees of success. Since the interfacial potential is fundamentally limited by interfacial exchange currents, it appears unlikely that such a material will ever exist. It is precisely this difficulty that has forced the majority of investigators to rely on conventional reference electrodes and miniaturize them for compatibility with the ISFET. As expected, such miniaturization is subject to trade-offs. As an example, to miniaturize the conventional liquid junction reference electrode, smaller internal reference solution volumes are required. However, to prevent diffusional losses, which alter the reference potential, higher liquid junction impedances are necessitated. Also, fabrication of a conventional liquid junction type reference electrode is usually not process compatible with planar fabrication techniques and therefore not easily integrated with the ISFET. Thin film metal depositions are process compatible and several investigations have involved the use of a thin film AG/AgCl electrode which is either in direct contact with a test solution of constant Cl− concentration or the Ag/AgCl is covered with a polymer saturated with a solution of Cl−. However, both types are severely restricted by the variance of the reference electrode potential to changing concentration of its primary ion.

An object of the present invention is to provide a miniature reference electrode of the liquid junction type which can be batch produced using planar integrated circuit technology.

Another object of the invention is to provide a fully integrated electrochemical sensor comprising an Ion Sensitive Field Effect Transistor and a liquid junction reference electrode integrated on the same chip.

The invention will now be described in more detail, by way of an example, in the following description with reference to the accompanying drawings in which:

FIG. 1.a shows a cross section view of a preferred embodiment of a reference electrode according to the invention;

FIG. 1.b shows a variant of the embodiment of FIG. 1.a;

FIG. 2 shows an ISFET structure with the reference electrode integrated on the same chip;

FIG. 1a shows a diagrammatic view in cross section of the reference electrode according to the invention. A flat substrate 1, which may be of silicon, is provided with a cavity 2. The cavity 2 is closed at one end by a thin membrane 3 made of porous silicon and at the other end by a cap 4, which may be a glass cover, anodically bonded to the substrate to hermetically close the cavity. Before closing, the cavity 2 is filled up with a liquid reference solution 5 which, by way of example, may be a saturated solution of potassium chloride (KCl). Also an electrode 6, for example of the type Ag/AgCl is provided to make an electrical connection between an outside voltage source (not shown) and the internal reference solution 5.

The basic idea of the present invention is the use of a porous silicon membrane forming a liquid junction to electrically connect the internal reference electrode solution to the external solution to be tested.

It is particularly advantageous, although not essential, that the substrate also be made of silicon material thus allowing known techniques to be used for producing both the cavity 2 and the porous silicon membrane 3.

The substrate material is an n-type silicon wafer with 20 millimeters thickness. At first, a hole is anisotropically etched in the back side of the wafer using a well known KOH etchant until the desired membrane thickness (10–70 $\mu$m) was reached. After the membrane is formed, aluminum is evaporated on the front side of the wafer to provide electrical connection to the silicon membrane. This silicon membrane is then anodized to porous silicon in Hydrofluoric acid (HF) solution at current densities between 20 and 100 mA/cm$^2$ and under illumination from an infrared filtered quartz iodide lamp. After anodization, the silicon membrane is permeated with a dense network of very fine pores, preferentially oriented in the direction of current flow. Pore diameter, and thus the porosity of the membrane, may be controlled by various processing parameters, such as anodization current, HF concentration and illumination. It is possible to produce pores with diameters varying from 10 nanometers to 1 micrometer, which corresponds to reference electrodes, with impedances ranging from several M.ohms to a few K.ohms. The reference electrode cavity is filled with saturated KCl solution and then hermetically sealed with a glass cover. Sealing may be done either by gluing or anodically bonding the glass cover to the substrate. Electrical contact to the internal reference solution is performed by means of a Ag/AgCl electrode. By way of example, this electrode can be realized by depositing on the glass cover, previously coated with a thin film of Titanium, an Ag layer of about 1 $\mu$m in thickness and then chemically anodizing the Ag layer in a HCl solution.

FIG. 1.b represents a variant of the reference electrode of FIG. 1.a. The same structure as in FIG. 1.a is shown except that the substrate 8 is made of an insulating material, such as sapphire, glass, ceramic, etc and the membrane 9 is formed by locally anodizing a silicon layer 7, which has been previously deposited on the substrate.

All steps of the process described above to produce a miniature reference electrode are fully compatible with technologies used to produce integrated chemical sensors such as ISFET's. Therefore, it is proposed according to the present invention to take advantage of that compatibility to implement both the sensor and the reference electrode on the same chip. A preferred embodiment of a completely integrated solid state sensor which combines the reference electrode of FIG. 1 with a CMOS ISFET, is shown in FIG. 2 in which elements, which are similar to those in FIG. 1, are denoted by the same reference numerals. The ISFET 10 is fabricated on the front side of an n-type silicon wafer 1, using standard metal-gate CMOS technology. The ISFET 10 is an n-channel MOSFET, the gate of which constitutes an ion-sensitive layer. The CMOS process produces p-well 13, $n^+$-source 12 and drain 11 diffusions. An oxide layer ($SiO_2$) is then grown to form the gate oxide 15a in the gate region and the field oxide 15b outside the gate region. The gate 16 is made of any suitable material for the application envisaged. For example in the event of a PH-sensor, the gate material may be silicon nitride, aluminum oxide or even the oxide layer 15a itself. Electrical connections (not shown) to source 12, drain 11, p-well 13, as well as to the substrate 1, are made by means of aluminum using well-known techniques. Both structure and fabrication process of ISFET's are well known by those skilled in the art so that a more detailed description is not necessary. After the ISFET has been fabricated, the reference electrode is added by means of the process previously described in relation with FIG. 1.

Although exemplary embodiments of the invention have been shown and described, it should be understood that many modifications can be made without departing from the spirit and scope of the invention. Accordingly, the invention is not limited by the foregoing description but only by the claims appended hereto.

What is claimed is:

1. A miniature reference electrode providing both electrical connection and a liquid junction between a reference liquid solution and a solution to be tested, comprising:
   a substrate provided with a cavity to hold said reference liquid solution;
   a membrane comprising porous silicon closing a first end of said cavity;
   means for applying fixed control voltage to said reference liquid solution; and
   means for hermetically closing a second end of said cavity.

2. A miniature reference electrode according to claim 1, wherein said substrate comprises insulating material.

3. A miniature reference electrode according to claim 1, wherein said substrate comprises silicon.

4. A miniature reference electrode according to claim 1, wherein said means for applying the fixed control voltage comprises an electrode disposed in said cavity.

5. A miniature reference electrode according to claim 1, wherein said means for hermetically closing said second end of the cavity comprises a glass cover which is sealed to said substrate.

6. A miniature reference electrode according to claim 5, wherein said means for applying the control voltage comprises an electrode formed on the surface of said glass cover.

7. An integrated chemical sensor including an Ion Sensitive Field Effect Transistor formed in a silicon substrate and a miniature reference electrode on said silicon substrate, wherein said electrode comprises:
   a cavity provided in said silicon substrate to hold a reference liquid solutiion;
   a membrane comprising porous silicon, said membrane closing a first end of said cavity;
   means for applying a fixed control voltage to said reference liquid solution; and
   means for hermetically closing a second end of said cavity.

8. An integrated sensor according to claim 7, wherein said porous silicon membrane is formed on the same side of said silicon substrate as the Ion Sensitive Field Effect Transistor.

* * * * *